United States Patent [19]

Erskine et al.

[11] Patent Number: 5,231,466
[45] Date of Patent: Jul. 27, 1993

[54] CAPILLARY FLUID STREAM CONCENTRATION MEASURING APPARATUS AND METHOD

[75] Inventors: Steven R. Erskine; Hernan J. Cortes; Yvonne M. Walbroehl; Curtis D. Pfeiffer, all of Midland, Mich.

[73] Assignee: Dow Chemical Company, Midland, Mich.

[21] Appl. No.: 739,278

[22] Filed: Aug. 1, 1991

[51] Int. Cl.$^5$ .............................................. G01B 9/02
[52] U.S. Cl. .................................... 356/354; 356/361; 356/128
[58] Field of Search ............... 356/253, 354, 361, 346, 356/128

[56] References Cited

U.S. PATENT DOCUMENTS

| | | |
|---|---|---|
| 2,568,589 | 9/1951 | Labhart. |
| 2,809,551 | 10/1957 | Svensson. |
| 2,866,377 | 12/1958 | Rantsch. |
| 2,896,502 | 7/1959 | Nordin. |
| 3,358,148 | 12/1967 | Conklin et al.. |
| 3,539,262 | 11/1970 | Pryor. |
| 3,680,963 | 8/1972 | Edwards et al. ............ 356/361 |
| 3,999,856 | 12/1976 | Unterleitner ............ 356/246 |
| 4,076,420 | 2/1978 | DeMaeyer et al.. |
| 4,640,615 | 2/1987 | Sasaki ............ 356/361 |
| 4,644,755 | 2/1987 | Esslinger et al.. |
| 4,690,562 | 9/1987 | Davies et al. ............ 356/361 |

FOREIGN PATENT DOCUMENTS 1318859 6/1987 U.S.S.R. ............... 356/361

OTHER PUBLICATIONS

Selected pages of Journal of Chromatorgraphy, vol. 30, Microcolumn Spearations, M. Novotny and D. Ishii, Elsevier, 1985.
Aids for Analytical Chemists, Simple Nanoliter Refractive Index Detector, Darryl J. Bornhop and Norman J. Dovichi, Univ. of Wyoming Laramie, Wyoming, 1986 Analytical Chemistry, vol. 58, No. 2,
Simultaneous Laser-Based Refractive Index and Absorbence Determinations within Micrometer Diameter Capillary Tubes, Darryl J. Bornhop and Norman J. Dovichi, Analytical Chemistry, 1987.
Journal of Chromatography, vol. 384, pp. 181-187 "Subnanoliter Laser-based Refractive Index Detector for 0.25 mm ID Microbore Liquid Chromatography".
Selected page from a book entitled Introduction to Modern Liquid Chromatorgraphy, Second Edition, John Wiley & Sons pp. 140-145.

Primary Examiner—Samuel A. Turner

[57] ABSTRACT

There is provided an apparatus for monitoring the relative concentration of an analyte in a fluid stream, with such apparatus including a capillary tube for containing the flowing fluid, optics for directing a single beam of monochromatic light through the capillary tube to produce a diffraction pattern having a number of interference fringes. A translatable photodiode is provided to monitor a portion of one of the fringes passing through a light limiting slit, whereby a signal proportional to the concentration of the analyte in the fluid is produced based upon the varying intensity of the monitored fringe. The capillary tube is preferably provided as a fused silica member having an inner flow diameter of 100 micrometers or less.

20 Claims, 2 Drawing Sheets

CAPILLARY FLUID STREAM CONCENTRATION MEASURING APPARATUS AND METHOD

TECHNICAL FIELD

This invention relates to a universal detection device and method for monitoring the concentration of a fluid stream for application in liquid separation techniques such as liquid chromatography and electrophoresis, and, more particularly, to a simplified monitoring device and method for dynamically monitoring the concentration of an analyte in an eluent flowing in a small diameter capillary tube.

BACKGROUND ART

It is often desirable to subject various liquids or other solutions to quantitative investigation by means of electrophoretic techniques, or other liquid separation techniques such as liquid chromatography. Many of these methods depend upon the measurement of the refractive index of the solution, and deduction of the distribution of the concentration of the relevant substances from the relative changes in refractive index monitor. Moreover, the trend in this industry has been driven by a consensus that smaller diameter flow columns provide higher separation efficiencies and reduce mobile phase usage.

To optimize the accuracy and reliability of the concentration monitoring devices and techniques, it is similarly necessary to utilize correspondingly small volumes of test fluids as well. The use of ever smaller capillary columns in various liquid separation techniques, however, has placed increased emphasis upon a need for miniaturization of refractive index detector technology. Apparatuses and techniques for measuring changes in the refractive index in small detection cells has not kept pace with the downsized capillary column developments.

For example, devices incorporating the interferometric method for determining the refractive index, such as devised by Mach and Zehnder, Michelson, and Jamin, are relatively complex. These methods require various plates and mirrors for separating and directing light beams through test and reference media, and sensitive adjustments which severely complicate and limit their applicability, especially in conjunction with small volume cells. U.S. Pat. No. 2,568,589, which issued to H. Labhart, attempted to address the shortcomings of the interferometric devices by providing a monochromatic light source directed against a plane parallel plate at an oblique angle to create two beams. A second plane parallel plate was arranged perpendicularly to the parallel light beams, and a test cell was arranged between the two plates and in line with one of the beams. The two beams were then compared by an optical system to produce an image of the test cell.

Similarly, U.S. Pat. No. 2,809,551, which issued to S. Svensson, utilizes an extended light source, and a half-transparent metal foil arranged between two congruent plane surfaces splits the beam of light so as to pass separately through a sample cell and a reference cell before being directed to a photographic plate. In addition to being relatively complex, these systems require two separate light beams and multiple passes of the light through the test medium held within a captive cell. More importantly, they were not readily adaptable to capillary separation schemes as required in modern operations.

An optical interferometer for high speed plasma diagnostics is shown in U.S. Pat. No. 3,539,262, which issued to T. Pryor. This device allegedly measures rapid phase changes in plasma due to electron density variations. Particularly, a laser beam is to be divided into two beams by a mirror beam splitter, and one of the beams passes through plasma held in a container. The other beam acts as a reference, and both beams are combined before passing through a slot and impinged on a photodiode. Electronics associated with the photodiode discriminate between the plasma light, noise, and phase shifted laser light passing through the plasma.

Similar split beam technology has also been applied to sample cuvettes for use with small volume capillary columns, such as for liquid chromatography and spectroscopic procedures. Particularly, a group of scientists from the University of Wyoming, recognizing that smaller volume capillary tubing produces a corresponding decrease in the detector volume, incorporated a beam splitter to direct a portion of a laser beam through a test cuvette having an inside diameter of approximately 100 micrometers, while passing the other beam directly to a reference photodiode. The first beam, having passed through the sample cell, was received by a photodiode identical with the reference photodiode, for a refractive index comparison. The cuvette was located on a three-axis translational stage to enable alignment with the laser beam, while the receiving photodiode was located on a single translation stage for movement perpendicular to the plane formed by the laser beam and the sample cuvette. The signal photodiode was then placed at the sharp boundary between the main beam and the first adjoining dark fringe created, and a strip chart recorder was utilized to monitor changes in the sample volume refractive index.

These experiments clearly recognized that the major limitation in capillary liquid chromatographic performance resided in the detector technology, and the difficulty in miniaturizing detector instrumentation without compromising its performance. Some of these same scientists performed other experiments at the University of Alberta, Edmonton, commenting upon the continuing problem in providing detector instrumentation having satisfactory performance with small tube capillary chromatography and electrophoresis. In these other tests, two separate laser light sources were provided and separately passed through a capillary test cuvette Capillary tubes having diameters of 50, 100 and 500 micrometers were tested, and a photodiode for monitoring the complicated beam profile was provided. The beam profile consisted of a set of diffraction fringes, and the photodiode was first located in the most intense portion of the beam profile, then translated perpendicularly to the beam axis such that the photodiode intensity was approximately 0.37 times the maximum intensity. It was recognized that while higher sensitivity could be obtained if the photodiode was receiving the most intense portion of the beam profile, linearity was compromised at higher intensity levels. Translation of the photodiode optimized sensitivity and linearity. It was found, however, that the smaller test cuvettes produced poorer refractive index performance, presumably due to temperature variations between the samples.

Consequently, while a great deal of effort has been directed to providing improved refractive index detection devices and procedures, heretofore there has not been provided a relatively universal detection device design which is easily adapted to small capillary diameters, which can provide adequate and dependable accuracy, and which can measure refractive index variations dynamically in a capillary flow tube used in liquid separation techniques.

DISCLOSURE OF THE INVENTION

It is an object of this invention to provide an apparatus for monitoring the relative concentration of an analyte in a flowing fluid stream in a simple, low cost, and reliable manner.

It is another object of the present invention to provide a relatively universal fluid stream concentration measuring apparatus and method which, while not limited thereto, is especially adaptable to small capillary diameters for dynamically measuring the concentration of a flowing fluid.

It is yet another object of the present invention to provide an apparatus and method for monitoring the concentration of an analyte in an eluent flowing through a small diameter capillary flow tube in a simple, low cost, yet accurate and reliable manner.

It is also an object of the present invention to provide an improved apparatus and method for measuring the change in refractive index of a fluid flowing through a small diameter capillary column, such as for use in liquid chromatography or electrophoresis.

In accordance with one aspect of the present invention, there is provided an apparatus for monitoring the relative concentration of an analyte in a fluid stream, with such apparatus including a capillary tube for containing the flowing fluid, optics for directing a single beam of monochromatic light through the capillary tube to produce a diffraction pattern having a number of interference fringes. A translatable photodiode is provided to monitor a portion of one of the fringes passing through a light limiting slit, whereby a signal proportional to the concentration of the analyte in the fluid is produced based upon the varying intensity of the monitored fringe. The capillary tube is preferably provided as an optically clear member having an inner flow diameter of 100 micrometers or less.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE INVENTION

Figure 1:
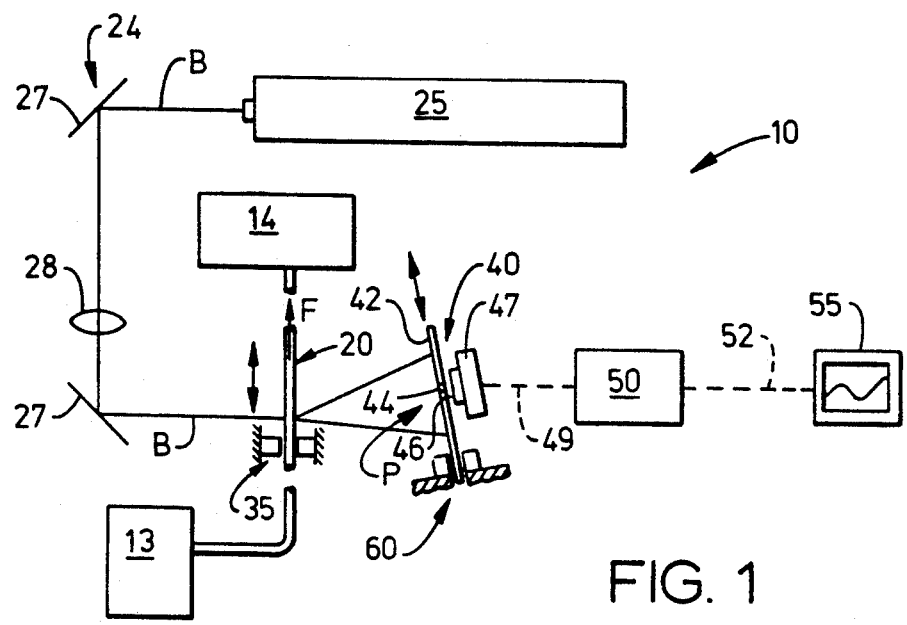
FIG. 1 is a schematic illustration of a monitoring apparatus made in accordance with the present invention.
Figure 4:
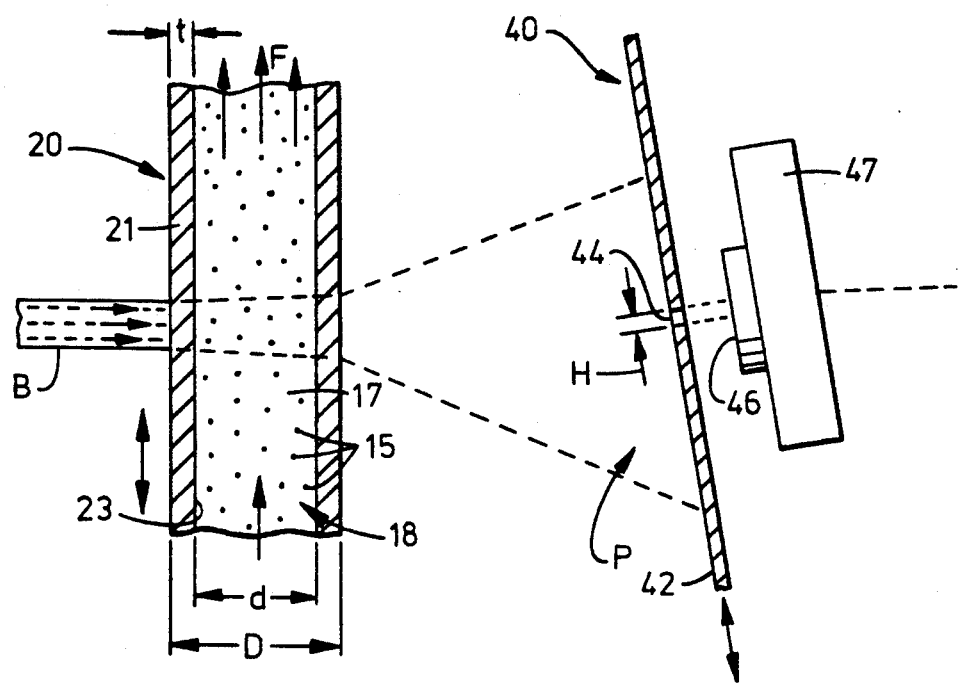
FIG. 4 is an enlarged cross-sectional view of a portion of the monitoring apparatus of FIG. 1, illustrating the capillary flow tube and the generation of the diffraction pattern in accordance with the present invention.

Referring now to the drawings in detail, wherein like numerals indicate the same elements throughout the views, FIG. 1 provides a schematic illustration of the basic components of a monitoring apparatus 10 made in accordance with the present invention. Particularly, monitoring apparatus 10 for monitoring the relative concentration of an analyte in a fluid stream or eluent (e.g. stream 18) flowing in the direction F as indicated in FIGS. 1 and 4. It is contemplated that the fluid to be monitored will comprise an analyte (e.g. analyte molecules 15) and a solvent (e.g. solvent 17), wherein the solvent will have a known and constant refractive index.

In continuing liquid separation techniques, it is desirable to continually monitor the relevant concentration of the analyte within the solvent. The present invention enables the dynamic monitoring of the relative concentration of an analyte within a capillary flow column intermediate a fluid reservoir 13 and a liquid separation device, such as a chromatograph 14. A detection capillary tube 20 which is optically clear at the particular laser light wavelength utilized having an inner diameter or flow channel 23 (see FIG. 4) for receiving the eluent stream 18 is preferably provided with a translation stage 35 to enable selective adjustment, as will be understood. As will be understood, it is preferred that capillary tube 20 have an index of refraction greater than the refractive index of the solvent in the fluid stream to simplify analysis. As used herein, the term "capillary tube" shall connote a tube of less than about one millimeter internal diameter.

Means 24 for directing a beam of monochromatic light through detection capillary 20 preferably comprises a solid state laser light source, such as the GaAlAs laser diode or the like. As used herein, the term "monochromatic light" shall be understood to comprise light having a bandpass (sometimes referred to as a bandpass width) of less than 10 nanometers (nm). It is preferred that the monochromatic light will have a bandpass of less than 0.001 nanometers, and it is believed that the invention will not function well if the bandpass exceeds 10 nanometers. In a particularly preferred embodiment, a laser light beam B having a pump wavelength of approximately 750 nanometers (nm), and a bandpass of about 0.001 nm is Provided, such as via the GaAlAs laser diode. Laser light sources provide light with substantially reduced optical noise, and a solid state laser source yields a more stable intensity, as well as obviating some inherent instabilities often encountered in common gas lasers, such as helium-neon lasers typically utilized.

Beam directing means 24 preferably comprises a pair of reflecting mirrors 27 to facilitate adjustment of beam alignment with detection capillary 20. A lens 28 is provided to focus beam B in a pencil beam fashion. For example, when utilized with a laser diode emitting a single beam light at a wavelength of approximately 750 nanometers, and 5 mW effective where the detection capillary 20 is arranged approximately 2 mm past the focal point (i.e., approximately 1 confocal parameter).

With eluent 18 flowing through detection capillary 20 (as illustrated in FIG. 4), capillary tube 20 is translated into the path of beam B until an extended diffraction pattern P having a plurality of interference fringes is created. As seen in FIGS. 1 and 4, diffraction pattern P propagates outwardly from capillary tube 20 toward template 42 spaced therefrom. It has been found that in the example described above, locating template 42 approximately 5 cm from capillary flow tube 20 enables the interference fringe pattern to spread slightly and to define a series of fairly well defined interference fringes 30 which impinge template 42, as illustrated best in FIG. 2.

In order to enable translation of the relative position of beam B and capillary flow tube 20 to create the extended diffraction pattern P, a translation stage device 35 is preferably provided to enable movement of capillary tube 20 along one or more axes. Particularly, movement in a direction normal to the path of beam B is most important to facilitate fine adjustment and alignment of beam B and tube 20. While it is recognized that either or both capillary tube 20 or beam B can be translated to adjust the relative position of these elements, it is preferred to minimize the necessary adjustment and movement of the laser beam optics.

Figure 2A:
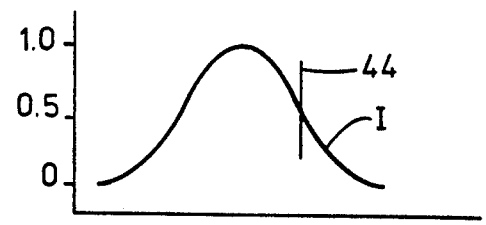
FIG. 2a is a graphical illustration of an exemplary intensity curve of a fringe response where light intensity is plotted along the vertical axis and the slit is positioned at the one-half response point.
Figure 2:
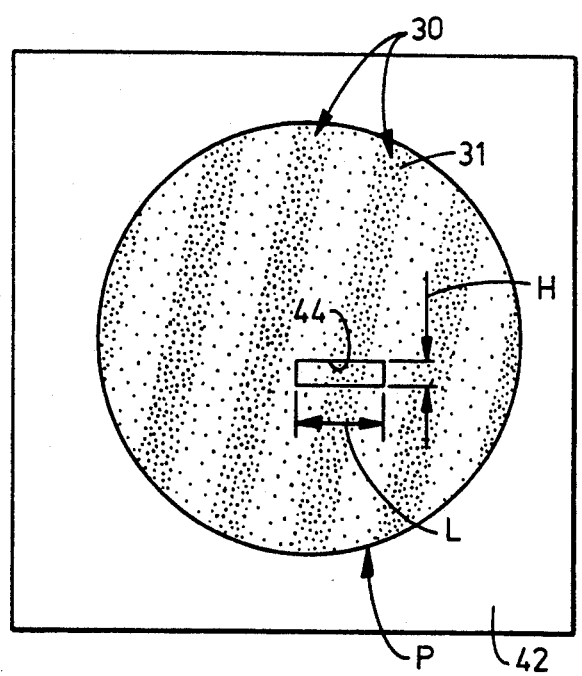
FIG. 2 is an enlarged plan view of an exemplary diffraction pattern having a plurality of interference fringes, as might be produced by directing the beam of monochromatic light through the capillary tube of a monitoring apparatus of the present invention.
Figure 3:
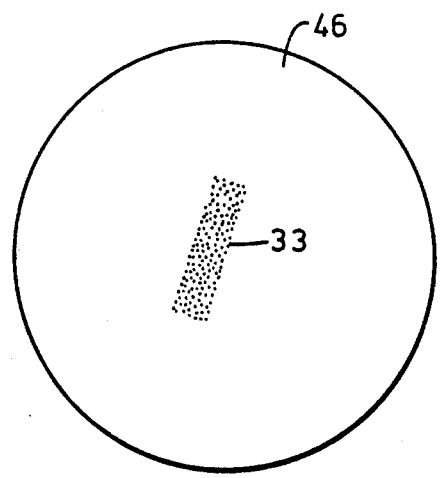
FIG. 3 is an enlarged illustration of the light receiving surface of a photodiode with a portion of one of the interference fringes of a diffraction pattern such as illustrated in FIG. 2 projected thereon.

Diffraction pattern P is extended from capillary tube 20 onto template 42, which includes a slit 44 having a length L and a height H, as best illustrated in FIG. 2. The size of slit 44 is preferably determined to isolate the amount of diffracted light which passes through template 42 for impingement upon light detector device 46. Light detector 46 can be any of a number of light sensitive devices such as photodiodes or photo multiplier tubes such as available from Hamamatsu Corporation, Middlesex, N.J. These detectors or laser sensing devices would, of course, be utilized in conjunction with support electronics (not shown) as described in the literature available in the trade from manufacturers such as Hamamatsu Corporation. The details of such support electronics are not critical to the present invention, so long as an output signal (e.g., 52) is provided which can be utilized by a data acquisition system 55, such as an oscilloscope, personal computer, strip chart recorder or the like.

FIG. 2 illustrates the extended diffraction pattern P as including a plurality of interference fringes 30. As mentioned, in use, capillary 20 is translated into the path of beam B until an extended diffraction pattern (e.g., P) is created. The position of capillary tube 20 can thereafter be adjusted by further translation until the intensity of the higher order fringes is maximized. Once this is done, slit 44 of template 42 can be translated into the extended diffraction pattern until a sampling of only a portion of the last observable fringe (e.g., 31) is isolated. In this way, only a portion of one or more (and preferably only one) selected fringes 31 passes template 42 and impinges on a 1 mm$^2$ photodiode 46.

As graphically illustrated in FIG. 2a, it is preferred that slit 44 be translated to a point along the last observable fringe (e.g., 31) where the intensity (I) of the fringe is about one-half of the maximum intensity of that fringe. It has been observed that the responsiveness of the monitored signal to the relative concentration of the analyte in the fluid is more linear when taken at the one-half response point. By maximizing the linearity of the response, the accuracy of the observed concentration is increased, and the need for digital signal processing and similar conversion procedures is eliminated.

By measuring only a small portion of the fringe pattern which passes slit 44, optical noise normally encountered in monitoring fringe patterns can also be reduced, while a relatively large refractive index response is maintained. Further, by utilizing only a small portion of the surface of the photodiode to measure light intensity changes, unwanted noise can be further minimized, while linearity and sensitivity are optimized, as mentioned above. Reduced optical noise permits more accurate monitoring, and allows the refractive index signal to be monitored dynamically and continuously.

Prior art devices and processes generally relied upon an averaging process wherein a number of refractive index signals were recorded over a predetermined time, then averaged to determine relative refractive index changes. Chromatographic detection requires accurate measurement of refractive index changes on an ongoing basis and with relatively fast time turnaround. The apparatus and method of the present invention enables substantially instantaneous and continuous monitoring of a flowing eluent, as well as applicability and adaptability to very small diameter capillary flow tubes. Moreover, it is contemplated that a capillary flow tube 20 of the present invention could be incorporated into the capillary column or flow cell of a liquid separation device, thereby obviating a need to provide separate testing cuvettes or similar detection cells. By eliminating separate or parallel testing devices and procedures, the liquid separation process can be simplified and optimized.

As seen best in FIG. 4, beam B is focused through capillary tube 20 such that it passes through tubular wall 21 having a known thickness t, through the flowing fluid stream 18, and toward the spaced template 42. The portion of the selected interference fringe 31 passing through slit 44 is Projected onto light detector 46. Support 47 may include various support electronics such as an amplifier, filter, or other known devices for receiving and processing the signal from photodiode 46 or similar light monitoring device to provide signal 52 to data acquisition system 55.

As the refractive index of the eluent 18 passing through flow channel 23 of capillary tube 20 changes, the refractive pattern produced will undergo a shift in position and/or intensity. These changes are monitored by measuring the intensity of light passing through slit 44 and incident on photodiode 46. The relative change in such intensity has been shown to be proportional to both the change in concentration of analyte 15 within the fluid stream 18, and the difference between the refractive index of analyte 15 and solvent 17. While such proportionality is both linear and nonlinear, as set forth herein, the linearity of the monitored response is optimized herein, and digital signal processing and/or similar conversion processes can be applied if desired or necessary.

Figure 5:
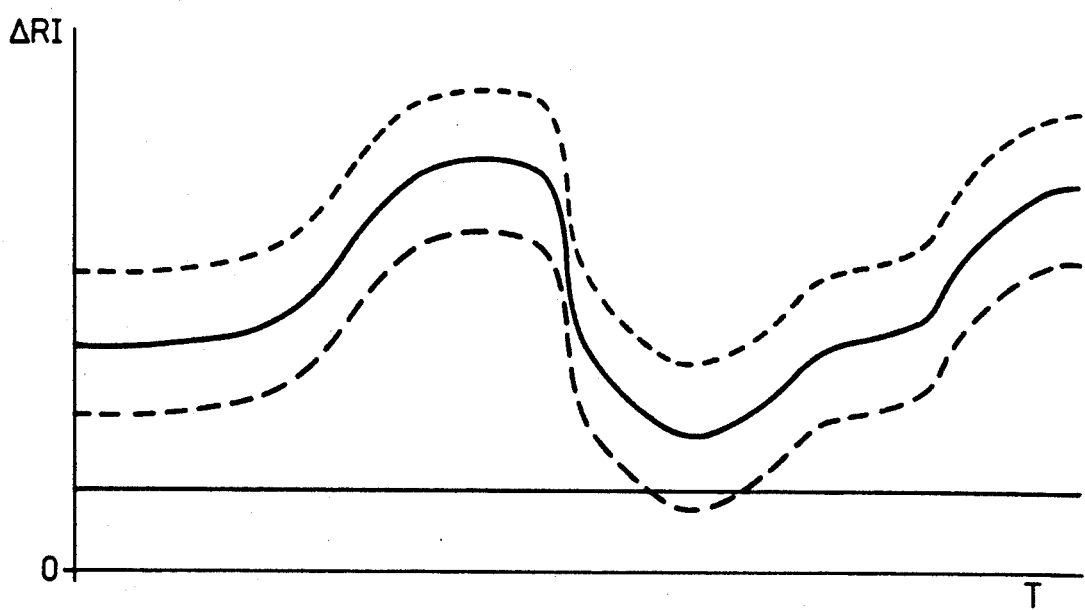
FIG. 5 is a graphical illustration in schematic form, illustrating the proportional relationship between the refractive index of an analyte in a flowing eluent, the light intensity of the monitored fringe, and the concentration of the analyte in a fluid comprising the analyte and a known solvent.

FIG. 5 graphically demonstrates the proportional relationship between the intensity of light monitored by apparatus 10, the refractive index changes of analyte 15 in the fluid stream, the relative concentration of analyte in the fluid, and the constant refractive index of solvent 17. As will be understood, the apparatus and method of the present invention is equally applicable to any type of separation scheme in which the index of refraction of an analyte differs from that of the solvent of the eluent stream. The detection accuracy using a 4 mW laser emitting light at 750 nanometers, wherein the inner diameter d of capillary tube 20 was 50 micrometers, has been shown to measure concentration levels of organic analytes as low as approximately 30 parts per million (ppm) in a detection volume of approximately 20 picoliters (pl). The proportionality response relationships are linear for analyte concentrations up to two orders of magnitude greater than the detection limit of this process. Consequently, highly accurate results can be consistently obtained in extremely small detection volumes, enabling optimal implementation of state of the art liquid separation techniques.

Having shown and described the preferred embodiments of the present invention, further adaptions of the concentration measuring apparatus and method described herein can be accomplished by appropriate modifications by one of ordinary skill in the art without departing from the scope of the present invention. Several of these potential modifications have been mentioned, and others will be apparent to those skilled in the art. For example, while the embodiments have been described with reference to capillary tubes, it is contemplated that the present invention can be similarly applied to equivalent arrangements such as flow cells having cylindrical windows. Accordingly, the scope of the present invention should be considered in terms of the following claims, and is understood not to be limited to the details of structure and operation shown and described in the specification and drawings.

We claim:

1. An apparatus for dynamically monitoring the relative concentration of an analyte in a flowing fluid stream comprising a capillary tube for containing a flowing fluid, means for directing a single beam of monochromatic light through a portion of said capillary tube to produce a diffraction pattern having a plurality of interference fringes, said directing means comprising means for translating said light beam and said capillary tube relative to one another to produce said diffraction pattern, means for monitoring only a selected portion of said fringes, and means for producing a single proportioned to said concentration of the analyte based upon said monitored fringe.

2. The apparatus of claim 1, wherein said capillary tube is optically clear at the wavelength of said monochromatic light.

3. The apparatus of claim 1, wherein said means for monitoring only a selected portion of said fringes comprises a template having a slit which restricts the amount of diffracted light which may pass through to a light detection device.

4. The apparatus of claim 1, wherein said means for monitoring comprises a detector upon which only a portion of a single selected interference fringe of said pattern is focused.

5. The apparatus of claim 4, further comprising a template, having a slit which can be translated relative to said diffraction pattern to isolate said portion of said selected interference fringe, and wherein said single selected interference fringe is the last observable fringe in the pattern.

6. The apparatus of calim 1, wherein said monochromatic light beam is provided by a solid state laser diode.

7. The apparatus of claim 1, wherein said capillary tube comprises a fused silica tubular conformation having an inner flow diameter of approximately 100 micrometers or less.

8. An apparatus for dynamically monitoring the relative concentration of an analyte in a flowing fluid stream, said apparatus comprising:
   a capillary tube for containing a flowing fluid stream;
   a single monochromatic light beam focused through a portion of said capillary tube for producing a diffraction pattern having a plurality of interference fringes;
   means for monitoring a selected portion of said diffraction pattern, said monitoring means comprising a template for limiting the amount of light passing to a monitor receiver, and means for adjusting the relative positions of said template and said diffraction pattern to isolate a selected interference fringe passing to said monitor receiver, and
   means for producing a signal proportional to the concentration of the analyte of said fluid stream and based upon the monitored fringe.

9. The apparatus of claim 8, wherein said capillary tube is substantially optically transparent to said monochromatic light and has an inner diameter of 100 micrometers or less.

10. The apparatus of claim 8, wherein said template includes a slit approximately 50 micrometers in width for limiting the amount of diffracted light passing to a light detector for monitoring intensity of said portion of a selected fringe.

11. The apparatus of claim 8, wherein said means for monitoring focuses a portion of the selected fringe upon a portion of a single selected interference fringe of said pattern.

12. The apparatus of claim 11, wherein said single selected interference fringe is the last observable fringe in the pattern.

13. The apparatus of claim 8, wherein said monochromatic light beam is provided by a solid state laser diode.

14. A method for dynamically monitoring the relative concentration of an analyte in a flowing fluid stream including the analyte and a solvent having an index of refraction different than that of said analyte, said method comprising the following steps:
   providing a flowing fluid in a capillary flow tube having an internal flow diameter of 100 micrometers or less;
   directing a beam of monochromatic light through a portion of said capillary tube;
   translating the relative positions of said beam and said capillary tube until an extended diffraction pattern having a plurality of fringes is produced;
   translating a template into said diffraction pattern such that only a sampling of a selected portion of said fringes is directed onto a monitoring device;
   monitoring the intensity of the selected portion of said fringes; and providing a signal proportional to the relative concentration of said analyte in the fluid stream based upon the monitored intensity of said fringe sampling.

15. The method of claim 14, wherein the monitoring step comprises directing the selected portion of said fringes passing through said template onto a photodiode.

16. The method of claim 14, wherein the step of monitoring the intensity of the fringes comprises focusing upon only a portion of a single selected interference fringe to monitor intensity variations as fluid flows through said capillary tube.

17. The method of claim 16, wherein said step of monitoring the intensity comprises focusing on the last observable fringe in the diffraction pattern at a Position where the intensity of that fringe is equal to one-half of the maximum intensity of such fringe.

18. The method of claim 15, wherein said template comprises a slit which, when translated to a desired position, allows only a portion of a single fringe to impinge the photodiode.

19. The method of claim 18, wherein only a portion of said single fringe is permitted to impinge on only a relatively small portion of the surface of the photodiode.

20. The apparatus of claim 8, further comprising means for translating said light beam and said capillary tube relative to one another, whereby the intensity of the higher order interference fringes of said diffraction pattern can be optimized.

* * * * *

UNITED STATES PATENT AND TRADEMARK OFFICE
CERTIFICATE OF CORRECTION

PATENT NO. : 5,231,466
DATED : July 27, 1993
INVENTOR(S) : Steven R. Erksine, Hernan J. Cortes, Yvonne M. Walbroehl
Curtis D. Pfeiffer It is certified that error appears in the above—identified patent and that said Letters Patent is hereby corrected as shown below:

In column 7, line 43, [claim 1], "single" should be deleted and replaced with --signal--

In column 8, line 55, [claim 14], "providing a signal proportional to the relative concentration of said analyte in the fluid stream based upon the monitored intensity of said fringe sampling", should begin a new paragraph within claim 14.

In column 9, line 3, [claim 17], "Position" should read --position--

Signed and Sealed this

Eighth Day of March, 1994

Attest:

BRUCE LEHMAN

*Attesting Officer*  *Commissioner of Patents and Trademarks*